(12) United States Patent
Furukawa et al.

(10) Patent No.: US 8,748,644 B2
(45) Date of Patent: Jun. 10, 2014

(54) RUTHENIUM COMPOUND, METHOD OF PRODUCING THE SAME, METHOD OF PRODUCING RUTHENIUM-CONTAINING THIN FILM USING THE SAME, AND RUTHENIUM-CONTAINING THIN FILM

(75) Inventors: Taishi Furukawa, Ayase (JP); Noriaki Oshima, Ayase (JP); Kazuhisa Kawano, Ayase (JP); Hirokazu Chiba, Ayase (JP)

(73) Assignee: Tosoh Corporation, Shunan-shi, Yamaguchi (JP)

( * ) Notice: Subject to any disclaimer, the term of this patent is extended or adjusted under 35 U.S.C. 154(b) by 15 days.

(21) Appl. No.: 13/129,589

(22) PCT Filed: Dec. 21, 2009

(86) PCT No.: PCT/JP2009/071256
§ 371 (c)(1),
(2), (4) Date: May 17, 2011

(87) PCT Pub. No.: WO2010/074037
PCT Pub. Date: Jul. 1, 2010

(65) Prior Publication Data
US 2011/0224453 A1  Sep. 15, 2011

(30) Foreign Application Priority Data

Dec. 25, 2008  (JP) ................ P2008-331172

(51) Int. Cl.
  C07F 17/02   (2006.01)
  B01J 31/00   (2006.01)
  C07F 15/00   (2006.01)
  B01J 31/22   (2006.01)

(52) U.S. Cl.
  CPC ........... *C07F 17/02* (2013.01); *C07F 15/0046* (2013.01); *B01J 31/2295* (2013.01)
  USPC ........................................ 556/136

(58) Field of Classification Search
  CPC .... C07F 15/0046; C07F 17/02; B01J 31/2295
  USPC ........................................ 556/136
  See application file for complete search history.

(56) References Cited

U.S. PATENT DOCUMENTS

| 2003/0088116 | A1   | 5/2003  | Kawano et al. |           |
|--------------|------|---------|---------------|-----------|
| 2005/0250341 | A1 * | 11/2005 | Itatani et al.| 438/763   |
| 2006/0211228 | A1 * | 9/2006  | Matsuda       | 438/575   |
| 2007/0072415 | A1 * | 3/2007  | Suzuki        | 438/652   |
| 2009/0035466 | A1 * | 2/2009  | Kawano et al. | 427/255.28|
| 2009/0130859 | A1 * | 5/2009  | Itatani et al.| 438/778   |

FOREIGN PATENT DOCUMENTS

| CN | 1408717 A       | 4/2003  |
|----|-----------------|---------|
| EP | 1 293 509 A2    | 3/2003  |
| JP | 2003-342286     | 12/2003 |
| JP | 2005-79118      | 3/2005  |
| JP | 2009-007270     | 1/2009  |
| JP | 2009-228113     | 10/2009 |
| WO | WO 2004/008513 A1 | 1/2004 |
| WO | 2005/103318     | 1/2005  |
| WO | WO 2006/101646 A1 | 9/2006 |
| WO | WO 2007/040704 A1 | 4/2007 |
| WO | WO 2007/058120 A1 | 5/2007 |
| WO | WO 2007/102333 A1 | 9/2007 |

OTHER PUBLICATIONS

International Search Report for PCT/JP2009/071256, mailed Feb. 2, 2010.
Shibutami et al. "A Novel Ruthenium Precursor for MOCVD without Seed Ruthenium Layer," *Tokyo Institute of Technology*, TOSOH Research & Technology Review, vol. 47 (2003) pp. 61-64.
Asano et al. "Fatigue-free $RuO_2/Pb(Zr,Ti)O_3/RuO_2$ capacitor prepared by metalorganic chemical vapor deposition at 395°C," *American Institute of Physics*, Applied Physics Letter, vol. 83, No. 26, Dec. 2003, pp. 5506-5508.
Shibutami et al. "Ruthenium Film with High Nuclear Density Deposited by MOCVD Using a Novel Liquid Precursor," *Electrochemical and Solid State Letters*, vol. 6, 2003, pp. C117-C119.
Kawano et al. "Seed Layer Free Conformal Ruthenium Film Deposition on Hole Substrates by MOCVD Using (2,4-Dimethylpentadienyl)(ethylcyclopentadienyl)ruthenium," *Electrochemical and Solid State Letters*, vol. 9, 2006, pp. C107-C109.
Kawano et al. "Conformability on Ruthenium Dioxide Films Prepared on Substrates with Capacitor Holes by MOCVD and Modification by Annealing," *Electrochemical and Solid State Letters*, vol. 9, 2006, pp. C175-C177.

(Continued)

*Primary Examiner* — Porfirio Nazario Gonzalez
(74) *Attorney, Agent, or Firm* — Nixon & Vanderhye P.C.

(57) ABSTRACT

This invention aims at providing (2,4-dimethylpentadienyl)-(ethylcyclopentadienyl)ruthenium which may contain its related structure compound, from which a ruthenium-containing thin film can be produced; a method of producing the same; a method of producing the ruthenium-containing thin film using the same; the ruthenium-containing thin film; and the like. The invention relates to producing the thin film using, as a precursor, (2,4-dimethylpentadienyl)(ethylcyclopentadienyl)ruthenium containing the related structure compound in an amount not more than 5% by weight, which can be obtained by separating the related structure compound from (2,4-dimethylpentadienyl)(ethylcyclopentadienyl)ruthenium containing the related structure compound.

1 Claim, 1 Drawing Sheet

(56) References Cited

OTHER PUBLICATIONS

Kawano et al. "Low-Temperature Preparation of Metallic Ruthenium Films MOCVD Using Bits (2,4-Dimethylpentadienyl)ruthenium," *Electrochemical and Solid State Letters*, vol. 10, 2007, pp. D60-D62.

Kim et al. "Atomic Layer Deposition of Ru Thin Films Using (2,4-Dimethylpentadienyl)(ethylcyclopentadienyl) Ru by a Liquid Injection System," *Journal of the Electrochemical Society*, vol. 154, 2007, pp. D-95-D-101.

Shibutami et al. "A Novel Ruthenium Precursor for MOCVD without Seed Ruthenium Layer," *Materials Research Society*, vol. 748, 2003, pp. 110-117.

Extended European Search Report in EP 09 83 4838 dated Jun. 15, 2012.

Chinese Office Action with English language translation in CN 200980152740.4 dated Apr. 12, 2013.

Office Action in EP 09 834 838.6 dated Oct. 16, 2013.

Taiwanese Office Action and English translation in TW098144688 dated Sep. 30, 2013.

Office Action and English translation in CN 200980152740.4 dated Dec. 27, 2013.

Notification of Reasons for Refusal and English translation in JP 2009-269219 dated Jan. 21, 2014.

\* cited by examiner

RUTHENIUM COMPOUND, METHOD OF PRODUCING THE SAME, METHOD OF PRODUCING RUTHENIUM-CONTAINING THIN FILM USING THE SAME, AND RUTHENIUM-CONTAINING THIN FILM

This application is the U.S. national phase of International Application No. PCT/JP2009/071256, filed 21 Dec. 2009, which designated the U.S. and claims priority to Japanese Patent Application No. 2008-331172, filed 25 Dec. 2008, the entire contents of each of which are hereby incorporated by reference.

TECHNICAL FIELD

The present invention relates to an organometallic compound useful for producing semiconductor devices, a method of producing the compound, a method of producing a metal-containing thin film using the organometallic compound, and a metal-containing thin film.

BACKGROUND ART

Scale down of memory cells is proceeding with the trend toward higher degrees of integration in semiconductor memory devices, and noble metals such as ruthenium, iridium, and platinum are being investigated as electrode materials for memory devices. For DRAM devices, among memory devices, ruthenium is regarded as a promising electrode material because oxides thereof also have electrical conductivity and because ruthenium has excellent suitability for processing for scale down. An optimal method for producing a ruthenium-containing thin film for use in highly integrated memory devices is a CVD (chemical vapor deposition) method from the standpoint of the excellent step coverage thereof.

Organometallic compounds are thought to be suitable as precursors for forming a thin film therefrom by a CVD method, because the compounds are easy to handle. At present, (2,4-dimethylpentadienyl)(ethylcyclopentadienyl)ruthenium (hereinafter referred to as DER) and the like are known as organometallic compounds for forming a thin ruthenium film or a thin ruthenium oxide film therefrom (see, for example, patent document 1 and non-patent documents 1 to 8).

It is generally known that, of a precursor fed to the step of thin-film formation in a CVD method, the amount of the precursor which is actually used for thin-film formation is 10% or less, and that most of the precursor which was fed is discarded without being utilized. It is desired to recover and reuse the precursor which is being discarded.

The present inventors have found that the precursor recovered after the step of thin-film formation using DER as a precursor contains, besides DER, DER related structure compounds which were generated from the DER by the heating conducted during the step of thin-film formation and that the precursor, as recovered, cannot be reused.

The DER related structure compounds differ from DER in property concerning thin-film formation and, hence, the same thin-film formation as from DER cannot be attained. Because of this, there are the cases where the DER which contains DER related structure compounds also cannot be used to conduct the same thin-film formation as from DER.

PRIOR-ART DOCUMENTS

Patent Document

Patent Document 1: JP-A-2003-342286

Non-Patent Documents

Non-Patent Document 1: *Tosoh Kenkyū/Gifutsu Hōkoku*, Vol. 47, pp. 61-64, 2003
Non-Patent Document 2: *Applied Physics Letters*, Vol. 83, No. 26, pp. 5506-5508, Dec. 29, 2003
Non-Patent Document 3: *Electrochemical and Solid-State Letters*, 6(9) C117-C119 (2003)
Non-Patent Document 4: *Electrochemical and Solid-State Letters*, 9(7) C107-C109 (2006)
Non-Patent Document 5: *Electrochemical and Solid-State Letters*, 9(11) C175-C177 (2006)
Non-Patent Document 6: *Electrochemical and Solid-State Letters*, 10(6) D60-D62 (2007)
Non-Patent Document 7: *Journal of The Electrochemical Society*, 154(2) D95-D101 (2007)
Non-Patent Document 8: *Mat. Res. Soc. Sytnp. Proc.*, Vol. 748, pp. 111-116, 2003

SUMMARY OF THE INVENTION

Problem that the Invention is to Solve

An object of the invention is to provide: DER from which a ruthenium-containing thin film can be produced although the DER contains one or more DER related structure compounds; a method of producing the DER; a method of producing a ruthenium-containing thin film using the DER; a ruthenium-containing thin film; and the like.

Means for Solving the Problem

The present inventors diligently made investigations in view of the current circumstances described above. As a result, the inventors have found that the object can be accomplished with DER which contains DER related structure compounds, so long as the content of the DER related structure compounds therein is 5% by weight or less. The invention has been thus completed.

Meanwhile, DER and the DER related structure compounds are akin in molecular weight, and both are bisdienyl-ruthenium compounds. These compounds are hence akin in chemical and physical properties, and it has usually been difficult to separate the compounds. The present inventors directed attention to a slight difference in chemical or physical property between the two kinds of compounds and have found that the object can be accomplished by separating the DER related structure compounds by distillation or a technique of liquid chromatography. The invention has been thus completed.

Namely, the invention provides DER characterized by containing one or more DER related structure compounds in an amount of 5% by weight or less. The invention further provides a method of producing DER which contains one or more DER related structure compounds in an amount of 5% by weight or less, the method being characterized by separating part of the DER related structure compounds from DER which contains DER related structure compounds. The invention furthermore provides a method of producing a ruthenium-containing thin film, the method being characterized by producing the thin film using, as a precursor, DER which contains one or more DER related structure compounds in an amount of 5% by weight or less. The invention still further provides a ruthenium-containing thin film characterized by being produced by the method.

Specifically, essential points of the invention reside in the following (1) to (6).

(1) (2,4-Dimethylpentadienyl)(ethylcyclopentadienyl)ruthenium characterized by containing one or more (2,4-dimethylpentadienyl)(ethylcyclopentadienyl)ruthenium related structure compounds in an amount of 5% by weight or less.

(2) The (2,4-dimethylpentadienyl)(ethylcyclopentadienyl)ruthenium according to (1) above, preferably characterized in that the (2,4-dimethylpentadienyl)(ethylcyclopentadienyl)ruthenium related structure compounds are bis(ethylcyclopentadienyl)ruthenium and/or (1,3-dimethylcyclopentadienyl)(ethylcyclopentadienyl)ruthenium.

(3) A method of producing the (2,4-dimethylpentadienyl)(ethylcyclopentadienyl)ruthenium according to (1) or (2) above, characterized by separating part of the (2,4-dimethylpentadienyl)(ethylcyclopentadienyl)ruthenium related structure compounds from (2,4-dimethylpentadienyl)(ethylcyclopentadienyl)ruthenium which contains one or more (2,4-dimethylpentadienyl)(ethylcyclopentadienyl)ruthenium related structure compounds.

(4) The method of production according to (3) above, preferably characterized in that the (2,4-dimethylpentadienyl)(ethylcyclopentadienyl)ruthenium related structure compounds are bis(ethylcyclopentadienyl)ruthenium and/or (1,3-dimethylcyclopentadienyl)(ethylcyclopentadienyl)ruthenium.

(5) A method of producing a ruthenium-containing thin film, characterized by producing the thin film using the (2,4-dimethylpentadienyl)(ethylcyclopentadienyl)ruthenium according to (1) or (2) above as a precursor.

(6) A ruthenium-containing thin film characterized by being produced by the method according to (5) above.

Effect of the Invention

The DER of the invention, which contains one or more DER related structure compounds in an amount of 5% by weight or less, can be used to form therefrom thin films equal to thin films formed from DER. The DER of the invention can be produced from DER which contains one or more DER related structure compounds by separating part of the DER related structure compounds from the DER. Consequently, DER which has been recovered from the step of thin-film formation by a CVD method and which contains DER related structure compounds can be reused according to the invention.

MODES FOR CARRYING OUT THE INVENTION

The invention is described below in detail.

In the invention, the term DER related structure compounds means bisdienylruthenium compounds other than DER, and the DER related structure compounds are not particularly limited. Examples thereof include bis(ethylcyclopentadienyl)ruthenium, (1,3-dimethylcyclopentadienyl)(ethylcyclopentadienyl)ruthenium, and bis(1,3-dimethylcyclopentadienyl)ruthenium. Of these DER related structure compounds, bis(ethylcyclopentadienyl)ruthenium and/or (1,3-dimethylcyclopentadienyl)(ethylcyclopentadienyl)ruthenium, which has an ethylcyclopentadienyl group, is important because of the miscibility thereof with DER. These related structure compounds are formed, as a result of severe heating of DER, by ligand exchange reactions or dehydrogenation reactions of DER or by consecutive reactions of products of these reactions. Examples of the "severe heating" include to heat DER at a temperature of 150° C. or higher, to use DER in a process for forming a thin film through coating fluid application, and to feed DER to a process for forming a thin film by a CVD method. However, the severe heating is not particularly limited.

In the invention, the expression "DER containing one or more DER related structure compounds in an amount of 5% by weight or less" means DER which contains one or more DER related structure compounds in such an amount in terms of weight percentage that [(DER related structure compounds)/((DER related structure compounds)+DER)]×100=5% by weight or less. It is essential that the DER of the invention should contain one or more DER related structure compounds, and DER which contains no DER related structure compound is outside the scope of the invention.

With respect to the amount of DER related structure compounds, DER which contains DER related structure compounds in an amount of 5% by weight can be used to form therefrom thin films equal to thin films formed from DER. However, DER which contains DER related structure compounds in an amount exceeding 5% by weight, e.g., 10% by weight, cannot be used to form therefrom thin films equal to thin films formed from DER. It is therefore essential that the amount of the DER related structure compounds contained in the DER should be 5% by weight or less. The amount thereof is preferably 3% by weight or less. There is no particular lower limit on the amount of the DER related structure compounds contained in the DER. However, in view of the fact that a detection limit in gas chromatography is 10 ppm, the lower limit of the amount of the DER related structure compounds may be about 10 ppm. From the standpoint of a balance between cost and operation time, etc., the lower limit thereof may be 0.5% or 1.0%.

The DER of the invention, which contains one or more DER related structure compounds in an amount of 5% by weight or less, may contain compounds other than DER and DER related structure compounds.

The DER of the invention, which contains one or more DER related structure compounds in an amount of 5% by weight or less, can be produced from DER which contains DER related structure compounds by separating part of the DER related structure compounds from the DER. In particular, it is preferred to separate part of the DER related structure compounds from DER which contains DER related structure compounds in an amount exceeding 5% by weight. It is more preferred to separate part of the DER related structure compounds from DER which contains DER related structure compounds in an amount which is more than 5% by weight but not more than 50% by weight. The method is suitable also for the separation of part of the DER related structure compounds from DER which contains DER related structure compounds and which has been recovered from the step of forming a thin film by a CVD method.

Examples of techniques for separating part of the DER related structure compounds from DER which contains DER related structure compounds include distillation or liquid chromatography. Of these techniques, liquid chromatography is preferred from the standpoint of ease of separating DER related structure compounds. Meanwhile, distillation is preferred from the standpoint of the ability to separate a large amount of a sample.

In the invention, the method of production through distillation may be conducted in the following manner. A mixture of DER and one or more DER related structure compounds is heated to vaporize the DER or the DER related structure compounds. Thereafter, the vaporized compound(s) are cooled and thereby liquefied, and the DER is recovered or part of the DER related structure compounds are removed, during the liquefaction. Thus, the DER of the invention, which contains one or more DER related structure compounds in an amount of 5% by weight or less, can be obtained. There is no limitation on the type of distillation apparatus which can be used, so long as the DER can be prevented from being excessively heated and thereby suffering changes with the lapse of time, e.g., decomposition. For example, use can be made of a distillation apparatus constituted of an evaporator and a distillation column. It is preferred to use a rectifier in order to improve separation performance. Whether the distillation method is batchwise or continuous is not limited, and the distillation may be conducted by either method. Use may also be made of a distillation apparatus in which a distillation part having the function of an evaporator has been integrated with a distillation column.

Meanwhile, the temperature within the distillation chamber is preferably 30° C. to 150° C., excluding 150° C., because at such temperatures, the DER can be prevented from decomposing and DER related structure compounds can be prevented from generating. The temperature within the distillation chamber is more preferably 40° C. to 130° C., especially preferably 50° C. to 110° C. The pressure within the evaporator is preferably 850 Pa or lower, more preferably 13 Pa or lower. In particular, it is preferred to employ conditions including a pressure of 1 Pa or lower, because at such pressures, the temperature within the evaporator can be lowered in order to inhibit DER decomposition. Pressures exceeding 850 Pa are undesirable because DER under such high-pressure conditions has a boiling point of 1.50° C. or higher, resulting in enhanced generation of decomposition by-products. By cooling the gas which has effused from the distillation column, the DER can be recovered. The cooling temperature in this operation is preferably −20° C. to 100° C. In the case where the cooling temperature is high, the amount of DER which is discharged without being liquefied is increased. On the other hand, low cooling temperatures may result in the cases where the DER solidifies and accumulates in the cooling part. Consequently, the cooling temperature is more preferably 10° C. to 40° C.

In the method of production by liquid chromatography in the invention, a mixture of DER and one or more DER related structure compounds is passed through a packing material together with an eluent, and part of the DER related structure compounds can be thereby separated. Examples of modes of liquid chromatography include the fixed bed mode, moving bed mode, and simulated moving bed mode, but the liquid chromatography is not particularly limited in mode. Examples of the packing material include porous polymers such as divinylbenzene polymers and styrene/divinylbenzene copolymers and alumina. However, the packing material is not particularly limited. When use is made of any of these packing materials, one packing material may be used alone or a mixture of two or more packing materials may be used. Examples of the eluent to be used when the mixture of DER is passed through the packing material include alcohols such as methanol, ethanol, and isopropanol; esters such as ethyl acetate and butyl acetate; halogenated hydrocarbons such as dichloromethane, chloroform, and carbon tetrachloride; and hydrocarbons such as pentane, hexane, cyclohexane, methylcyclohexane, ethylcyclohexane, heptane, octane, toluene, and xylene. When use is made of any of these eluents, one eluent may be used alone or a mixture of two or more eluents which are miscible with each other may be used. Preferred of these eluents from the standpoint of eluent polarity are hydrocarbons such as pentane, hexane, heptane, octane, and cyclohexane. From the standpoint of cost, hexane is most preferred.

A ruthenium-containing thin film can be produced using the DER of the invention, which contains one or more DER related structure compounds in an amount of 5% by weight or less, as a precursor. When the DER containing one or more DER related structure compounds in an amount of 5% by weight or less is to be used as a precursor to form a ruthenium-containing thin film on a substrate by a CVD method, the precursor is gasified and fed to over the substrate. Examples of methods for the gasification include: a method in which an inert carrier gas is introduced into the heated precursor and the precursor is introduced, in the state of accompanying the carrier gas, into a reaction chamber in which a substrate has been placed; or a method in which either the precursor as it is or a solution prepared by dissolving the precursor in an organic solvent is sent to a vaporizer and gasified in the vaporizer, and the gasified precursor is introduced into a reaction chamber in which a substrate has been placed.

Examples of the organic solvent for dissolving the precursor therein include alcohols such as methanol, ethanol, and isopropanol; esters such as ethyl acetate, butyl acetate, and isoamyl acetate; glycol ethers such as ethylene glycol monomethyl ether, ethylene glycol monoethyl ether, and ethylene glycol monobutyl ether; ethers such as glyme, diglyme, triglyme, and tetrahydrofuran; ketones such as methyl butyl ketone, methyl isobutyl ketone, ethyl butyl ketone, dipropyl ketone, diisobutyl ketone, methyl amyl ketone, and cyclohexanone; and hydrocarbons such as hexane, cyclohexane, methylcyclohexane, ethylcyclohexane, heptane, octane, toluene, and xylene. However, the organic solvent is not particularly limited.

Examples of the ruthenium-containing thin film are as follows. In the case where the DER of the invention, which contains one or more DER related structure compounds in an amount of 5% by weight or less, is used alone, a thin film of ruthenium metal, a thin film of a ruthenium oxide, or the like is obtained as the ruthenium-containing thin film. In the case where the DER of the invention is used in combination with another metallic precursor, a ruthenium-containing composite thin film is obtained. For example, when the DER of the invention is used in combination with a strontium precursor, an $SrRuO_3$ film is obtained. However, the composite thin film is not limited to this example. Examples of the strontium precursor include bis(dipivaloylmethanato)strontium and diethoxystrontium. However, the strontium precursor is not limited to these examples. In the case where the DER of the invention is used in combination with another metallic precursor, the precursors may be separately fed or may be mixed together and then fed. The CVD method to be used for forming the ruthenium-containing thin film of the invention is not particularly limited so long as the method is a CVD method in general use, such as thermal CVD, plasma-assisted CVD, photo-CVD, or an ALD method.

According to the invention, even DER which contains DER related structure compounds can be used to form therefrom thin films which are equal to thin films formed from DER, so long as the content of the DER related structure compounds therein is 5% by weight or less.

Furthermore, according to the invention, DER which contains one or more DER related structure compounds in an amount of 5% by weight or less can be produced from DER which contains one or more DER related structure compounds and which has been recovered from the step of forming a thin film by a CVD method, by separating part of the DER related structure compounds from the recovered DER, and the DER which contains one or more DER related structure compounds in an amount of 5% by weight or less can be reused as a precursor in the step of thin-film formation by a CVD method, thereby producing a ruthenium-containing thin film.

EXAMPLES

The invention will be explained below in detail by reference to Examples, but the invention should not be construed as being limited to the following Examples.

Incidentally, 1,3-dimethylcyclopentadiene, which was used for the synthesis of (1,3-dimethylcyclopentadienyl)(ethylcyclopentadienyl)ruthenium (hereinafter referred to as cyclization compound), can be synthesized by methylating 3-methyl-2-cyclopentenone and then dehydrating the methylated compound, with reference to a known method (e.g., *Inorganic Chemistry*, Vol. 15, No. 2, p. 466 (1976)).

Reference Example 1

Synthesis of (1,3-Dimethylcyclopentadienyl)(ethylcyclopentadienyl)ruthenium

In an argon atmosphere, 3.0 mL of 1,3-dimethylcyclopentadiene and 3.0 mL of ethylcyclopentadiene were added to a solution prepared by dissolving 0.51 g of ruthenium chloride hydrate in 40 mL of ethanol. Thereafter, 4.1 g of a zinc powder was added thereto. The mixture was stirred at 70° C. for 3 hours. The solvent was distilled off under vacuum, and hexane was added to the residue. The insoluble matter was removed by filtration, and the solvent was thereafter distilled off under vacuum. The resultant residue was distilled and then separated with an alumina column. Thus, 0.24 g of a yellow liquid was obtained (yield, 43%).

$^1$H NMR (500 MHz, CDCl$_3$, δ/ppm)
4.46 (s, 1H), 4.37 (t, J=1.5 Hz, 2H), 4.35 (d, J=1.0 Hz, 2H), 4.32 (t, J=1.5, 2H), 2.17 (q, J=7.5 Hz, 2H), 1.88 (s, 6H), 1.10 (t, J=7.5 Hz, 3H).

Example 1

Figure 1:
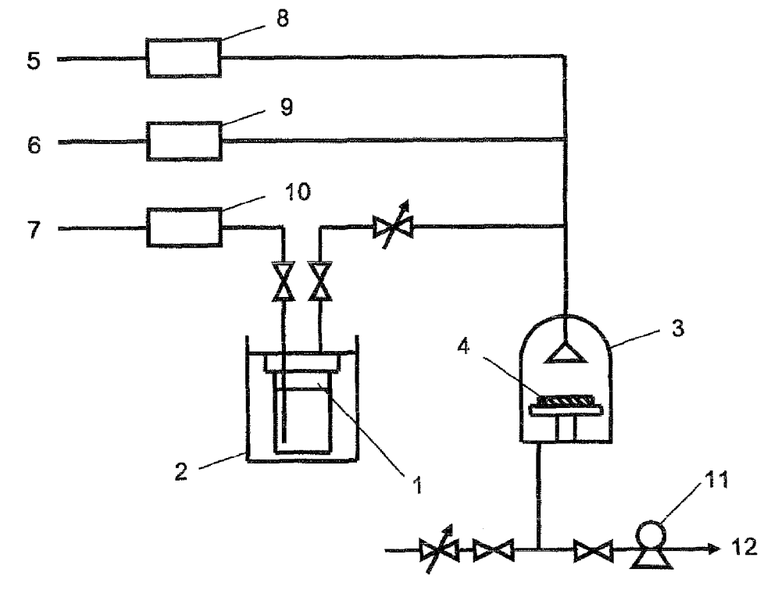
FIG. 1 is a view illustrating the CVD apparatus used in Examples and Comparative Examples.

A mixture composed of 5% by weight the cyclization compound and 95% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Example 2

A mixture composed of 2% by weight the cyclization compound and 98% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Comparative Example 1

A mixture composed of 10% by weight the cyclization compound and 90% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. As a result, no thin film was deposited on the substrate.

Comparative Example 2

A mixture composed of 12% by weight bis(ethylcyclopentadienyl)ruthenium and 88% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. As a result, no thin film was deposited on the substrate.

Example 3

A mixture composed of 5% by weight bis(ethylcyclopentadienyl)ruthenium and 95% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Example 4

A mixture composed of 3% by weight bis(ethylcyclopentadienyl)ruthenium and 97% by weight DER was used as a precursor to conduct film deposition on an SiO$_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas (O$_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Comparative Example 3

A mixture composed of 5% by weight the cyclization compound, 4% by weight bis(ethylcyclopentadienyl)ruthenium, and 91% by weight DER was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas ($O_2$) flow rate of 0.16 sccm, a substrate temperature of 300° C., and a pressure within the reaction chamber of 10 Torr. As a result, no thin film was deposited on the substrate.

Example 5

A mixture composed of 1% by weight the cyclization compound, 4% by weight bis(ethylcyclopentadienyl)ruthenium, and 95% by weight DER was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 scent, a reactant gas ($O_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Example 6

A mixture composed of 1% by weight the cyclization compound, 1% by weight bis(ethylcyclopentadienyl)ruthenium, and 98% by weight DER was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas ($O_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Example 7

Into a 30-mL eggplant type flask was introduced 8.7 g of a liquid DER mixture containing 20% by weight the cyclization compound and 20% by weight bis(ethylcyclopentadienyl)ruthenium. A Vigreux column, a Leibig condenser, and a thermometer were attached to the flask, and the atmosphere in the apparatus was replaced with argon. This apparatus was evacuated to $3\times10^{-2}$ Pa. Thereafter, the eggplant type flask was heated to 100° C. in stages. A 7.8-g portion of the sample which had been cooled with the Leibig condenser was removed as an initial distillate, and a 0.3-g portion of the sample was thereafter recovered as a main distillate. This main distillate of the sample was examined for the concentrations of the cyclization compound, bis(ethylcyclopentadienyl)ruthenium, and DER by gas chromatography. As a result, the concentrations thereof were found to be 1% by weight, 1% by weight, and 98% by weight, respectively, showing that DER was able to be separated from the DER related structure compounds.

Example 8

Into a 30-mL eggplant type flask was introduced 7.8 g of a liquid DER mixture containing 9% by weight the cyclization compound and 8% by weight bis(ethylcyclopentadienyl)ruthenium. A Vigreux column, a Leibig condenser, and a thermometer were attached to the flask, and the atmosphere in the apparatus was replaced with argon. This apparatus was evacuated to $3\times10^{-2}$ Pa. Thereafter, the eggplant type flask was heated to 100° C. in stages. A 3.6-g portion of the sample which had been cooled with the Leibig condenser was removed as an initial distillate, and a 3.2-g portion of the sample was thereafter recovered as a main distillate. This main distillate of the sample was examined for the concentrations of the cyclization compound, bis(ethylcyclopentadienyl)ruthenium, and DER by gas chromatography. As a result, the concentrations thereof were found to be 1% by weight, 2% by weight, and 97% by weight, respectively, showing that DER was able to be separated from the DER related structure compounds.

Example 9

Into a 100-mL eggplant type flask was introduced 23.2 g of a liquid DER mixture containing 9% by weight the cyclization compound and 8% by weight bis(ethylcyclopentadienyl)ruthenium. A Vigreux column, a Leibig condenser, and a thermometer were attached to the flask, and the atmosphere in the apparatus was replaced with argon. This apparatus was evacuated to $3\times10^{-2}$ Pa. Thereafter, the eggplant type flask was heated to 100° C. in stages. A 12.6-g portion of the sample which had been cooled with the Leibig condenser was removed as an initial distillate, and a 9.8-g portion of the sample was thereafter recovered as a main distillate. This main distillate of the sample was examined for the concentrations of the cyclization compound, bis(ethylcyclopentadienyl)ruthenium, and DER by gas chromatography. As a result, the concentrations thereof were found to be 2% by weight, 3% by weight, and 95% by weight, respectively, showing that DER was able to be separated from the DER related structure compounds.

Example 10

Using hexane solvent, 13 mg of a liquid DER mixture containing 9% by weight the cyclization compound and 8% by weight bis(ethylcyclopentadienyl)ruthenium was passed through a column having an inner diameter of 7.5 mm and a length of 30 cm and packed with a divinylbenzene polymer. A fraction was obtained from the eluate separated into fractions, and the solvent was thereafter removed therefrom to recover 3 mg of ruthenium complexes. The recovered ruthenium complexes were examined for the concentrations of the cyclization compound, bis(ethylcyclopentadienyl)ruthenium, and DER by gas chromatography. As a result, the concentrations thereof were found to be 1% by weight, 1% by weight, and 98% by weight, respectively, showing that DER was able to be separated from the DER related structure compounds.

Example 11

Using hexane solvent, 13 mg of a liquid DER mixture containing 9% by weight the cyclization compound and 8% by weight bis(ethylcyclopentadienyl)ruthenium was passed through a column having an inner diameter of 7.5 mm and a length of 30 cm and packed with alumina. A fraction was obtained from the eluate separated into fractions, and the solvent was thereafter removed therefrom to recover 2 mg of ruthenium complexes. The recovered ruthenium complexes were examined for the concentrations of the cyclization compound, bis(ethylcyclopentadienyl)ruthenium, and DER by gas chromatography. As a result, the concentrations thereof were found to be 1% by weight, 1% by weight, and 98% by weight, respectively, showing that DER was able to be separated from the DER related structure compounds.

Example 12

Using hexane solvent, 100 mg of a mixture composed of DER and the cyclization compound in a molar ratio of 7.6/1 was passed through a simulated moving bed type apparatus for liquid chromatography which included eight columns connected to each other, the columns each having an inner diameter of 7.8 mm and a length of 8 cm and packed with alumina. As a result, a hexane solution of a mixture composed of DER and the cyclization compound in a molar ratio of 21/1 was obtained as a strongly adsorbable component, and a hexane solution of a mixture composed of DER and the cyclization compound in a molar ratio of 0.09/1 was obtained as a weakly adsorbable component. It was thus found that DER was able to be separated from the cyclization compound.

Example 13

The liquid DER mixture obtained in Example 9, which contained 5% by weight DER related structure compounds, was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas ($O_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Comparative Example 4

Fresh DER (i.e., DER which was not one recovered from the step of forming a thin film by a CVD method) was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas ($O_2$) flow rate of 0.16 scent, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

Comparative Example 5

The cyclization compound was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 seem, a precursor pressure of 100 Torr, a diluent gas (Ar) flow rate of 170 sccm, a reactant gas ($O_2$) flow rate of 0.16 sccm, a substrate temperature of 300° C., and a pressure within the reaction chamber of 10 Torr. As a result, no thin film was deposited on the substrate.

Comparative Example 6

Bis(ethylcyclopentadienyl)ruthenium was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 seem, a reactant gas ($O_2$) flow rate of 0.16 sccm, a substrate temperature of 300° C., and a pressure within the reaction chamber of 10 Torr. As a result, no thin film was deposited on the substrate.

Comparative Example 7

DER was used as a precursor to conduct thin-film formation by a CVD method, and a liquid DER mixture containing 8% by weight the cyclization compound and 5% by weight bis(ethylcyclopentadienyl)ruthenium was recovered from the gas resulting from the step of thin-film formation. This liquid DER mixture was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 sccm, a reactant gas ($O_2$) flow rate of 0.16 sccm, a substrate temperature of 300° C., and a pressure within the reaction chamber of 10 Torr. As a result, no thin film was deposited on the substrate.

Example 14

DER was used as a precursor to conduct thin-film formation by a CVD method, and a liquid DER mixture containing 8% by weight the cyclization compound and 5% by weight bis(ethylcyclopentadienyl)ruthenium was recovered from the gas resulting from the step of thin-film formation. Into a 30-mL eggplant type flask was introduced 13.6 g of the liquid DER mixture. A Vigreux column, a Leibig condenser, and a thermometer were attached to the flask, and the atmosphere in the apparatus was replaced with argon. This apparatus was evacuated to $3\times10^{-2}$ Pa. Thereafter, the eggplant type flask was heated to 100° C. in stages. A 5.8-g portion of the sample which had been cooled with the Leibig condenser was removed as an initial distillate, and a 6.7-g portion of the sample was thereafter recovered as a main distillate. This main distillate of the sample was examined for the concentrations of the cyclization compound, bis(ethylcyclopentadienyl)ruthenium, and DER by gas chromatography. As a result, the concentrations thereof were found to be 2.5% by weight, 2.5% by weight, and 95% by weight, respectively, showing that DER was able to be separated from the DER related structure compounds.

Example 15

DER was used as a precursor to conduct thin-film formation by a CVD method, and a liquid DER mixture containing 8% by weight the cyclization compound and 5% by weight bis(ethylcyclopentadienyl)ruthenium was recovered from the gas resulting from the step of thin-film formation. Using hexane solvent, 13 mg of the liquid DER mixture was passed through a column having an inner diameter of 7.5 mm and a length of 30 cm and packed with alumina. A fraction was obtained from the eluate separated into fractions, and the solvent was thereafter removed therefrom to recover 1 mg of ruthenium complexes. The recovered ruthenium complexes were examined for the concentrations of the cyclization compound, bis(ethylcyclopentadienyl)ruthenium, and DER by gas chromatography. As a result, the concentrations thereof were found to be 1% by weight, 1% by weight, and 98% by weight, respectively, showing that DER was able to be separated from the DER related structure compounds.

Example 16

The liquid DER mixture obtained in Example 14, which contained 2.5% by weight the cyclization compound and 2.5% by weight bis(ethylcyclopentadienyl)ruthenium, was used as a precursor to conduct film deposition on an $SiO_2$/Si substrate for 1 hour by a CVD method using the apparatus of FIG. 1 under the conditions of a precursor temperature of 60° C., a carrier gas (Ar) flow rate of 30 sccm, a precursor pressure of 100 Torr, a diluent gas (Ar) flow rate of 170 seem, a reactant gas ($O_2$) flow rate of 0.16 sccm, a substrate temperature of 300° C., and a pressure within the reaction chamber of 10 Torr. The thin film produced was examined by fluorescent X-ray spectroscopy and, as a result, a characteristic X-ray assigned to ruthenium was observed. The film was examined for thickness with an SEM. As a result, the film thickness was found to be 40 nm.

The following can be understood from the Examples and Comparative Examples given above.

1) From a comparison between Comparative Example 4 and Comparative Example 5 and from a comparison between Comparative Example 4 and Comparative Example 6, it can be seen that DER differs from the DER related structure compounds in property concerning thin-film formation. From a comparison between Comparative Example 4 and Comparative Example 7, it can be seen that the DER recovered after the step of forming a thin film by a CVD method contains DER related structure compounds which have come thereinto and, hence, the recovered DER cannot be used to form a ruthenium-containing film therefrom although any scientific cause of the inhibition of thin-film formation cannot be specified. From a comparison between Comparative Example 4 and Comparative Example 1, it can be seen that since the DER which contains 10% by weight the cyclization compound cannot be used to form a thin film therefrom, this DER differs from the fresh DER in property concerning thin-film formation. From a comparison between Comparative Example 4 and Example 1 and from a comparison between Comparative Example 4 and Example 2, it can be seen that the DER which contains the cyclization compound in an amount of 5% by weight or less can form a thin film equal to the thin film formed from the fresh DER.

From a comparison between Comparative Example 4 and Comparative Example 2, it can be seen that since the DER which contains 12% by weight bis(ethylcyclopentadienyl) ruthenium cannot be used to form a thin film therefrom, this DER differs from the fresh DER in property concerning thin-film formation. From a comparison between Comparative Example 4 and Example 3 and from a comparison between Comparative Example 4 and Example 4, it can be seen that the DER which contains bis(ethylcyclopentadienyl)ruthenium in an amount of 5% by weight or less can form a thin film equal to the thin film fainted from the fresh DER. From a comparison between Comparative Example 4 and Comparative Example 3, it can be seen that since the DER which contains 5% by weight the cyclization compound and 4% by weight bis(ethylcyclopentadienyl)ruthenium, i.e., the DER containing 9% by weight DER related structure compounds, cannot be used to form a thin film therefrom, this DER differs from the fresh DER in property concerning thin-film formation. From a comparison between Comparative Example 4 and Example 5 and from a comparison between Comparative Example 4 and Example 6, it can be seen that the DER which contains 1% by weight the cyclization compound and 4% by weight bis(ethylcyclopentadienyl)ruthenium or the DER which contains 1% by weight the cyclization compound and 1% by weight bis(ethylcyclopentadienyl)ruthenium, i.e., the DER containing DER related structure compounds in an amount of 5% by weight or less, can form a thin film equal to the thin film formed from the fresh DER.

2) From a comparison between Example 13 and Comparative Example 4, it can be seen that there is no difference in thin-film formation between the fresh DER and the DER in which the content of DER related structure compounds has been reduced to 5% by weight or less by separating part of the DER related structure compounds.

3) It can be seen from Examples 14 and 15 that DER which contains DER related structure compounds in an amount of 5% by weight or less is obtained from the DER which contains DER related structure compounds and has been recovered from the step of forming a thin film by a CVD method, by separating part of the DER related structure compounds by distillation or liquid chromatography. Furthermore, from a comparison between Example 16 and Comparative Example 4, it can be seen that there is no difference in thin-film formation between the DER thus obtained, which contains DER related structure compounds in an amount of 5% by weight or less, and the fresh DER.

While the invention has been described in detail and with reference to specific embodiments thereof, it will be apparent to one skilled in the art that various changes and modifications can be made therein without departing from the spirit and scope thereof.

This application is based on a Japanese patent application filed on Dec. 25, 2008 (Application No. 2008-331172) and a Japanese patent application filed on Nov. 26, 2009 (Application No. 2009-269219), the contents thereof being incorporated herein by reference.

INDUSTRIAL APPLICABILITY

The DER of the invention, which contains one or more DER related structure compounds in an amount of 5% by weight or less, can form thin films equal to thin films formed from DER. The DER of the invention can be produced from DER which contains one or more DER related structure compounds by separating part of the DER related structure compounds from the DER. Consequently, DER which contains DER related structure compounds and which has been recovered from the step of thin-film formation by a CVD method can be reused according to the invention. Therefore, the invention has a significant industrial value.

DESCRIPTION OF THE REFERENCE NUMERALS

1. Precursor vessel
2. Thermostatic chamber

3. Reaction chamber
4. Substrate
5. Reactant gas
6. Diluent gas
7. Carrier gas
8. Mass flow controller
9. Mass flow controller
10. Mass flow controller
11. Vacuum pump
12. Exhaust gas

The invention claimed is:
1. A composition consisting essentially of:
(2,4-dimethylpentadienyl)(ethylcyclopentadienyl)ruthenium and any one or more of:
bis(ethylcyclopentadienyl)ruthenium,
(1,3-dimethylcyclopentadienyl)(ethylcyclopentadienyl)ruthenium, and
bis(1,3-dimethylcyclopentadienyl)ruthenium
present in the composition in an amount of up to 5% by weight.

* * * * *